United States Patent
Chen et al.

(10) Patent No.: US 12,391,666 B2
(45) Date of Patent: Aug. 19, 2025

(54) INDOLINE-1-FORMAMIDE COMPOUND, PREPARATION METHOD THEREFOR, AND MEDICAL USE THEREOF

(71) Applicant: Beijing Innocare Pharma Tech Co., Ltd., Beijing (CN)

(72) Inventors: Xiangyang Chen, Beijing (CN); Yucheng Pang, Beijing (CN); Yingxiang Gao, Jiangsu (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 1048 days.

(21) Appl. No.: 17/055,425

(22) PCT Filed: May 9, 2019

(86) PCT No.: PCT/CN2019/086241
§ 371 (c)(1),
(2) Date: Nov. 13, 2020

(87) PCT Pub. No.: WO2019/218928
PCT Pub. Date: Nov. 21, 2019

(65) Prior Publication Data
US 2021/0188806 A1    Jun. 24, 2021

(30) Foreign Application Priority Data
May 15, 2018   (CN) .......................... 201810459147.5

(51) Int. Cl.
*C07D 401/12*   (2006.01)
*A61P 35/00*   (2006.01)
*C07D 413/14*   (2006.01)

(52) U.S. Cl.
CPC ............ *C07D 401/12* (2013.01); *A61P 35/00* (2018.01); *C07D 413/14* (2013.01)

(58) Field of Classification Search
CPC ...... C07D 401/12; C07D 413/14; A61P 35/00
See application file for complete search history.

(56) References Cited

U.S. PATENT DOCUMENTS

| 7,253,286 B2 * | 8/2007 | Funahashi ............ A61K 31/517 546/153 |
| 2004/0053908 A1 | 3/2004 | Funahashi et al. |

FOREIGN PATENT DOCUMENTS

| CN | 101024627 A | 8/2007 |
| EP | 3293177 A1 | 3/2018 |
| JP | 2012511535 A | 5/2012 |
| WO | WO-2002/032872 A1 | 4/2002 |
| WO | WO-2004043379 A2 | 5/2004 |
| WO | WO-2005073224 A2 | 8/2005 |
| WO | WO-2007/146824 A2 | 12/2007 |
| WO | WO-2015088847 A1 | 6/2015 |
| WO | WO-2016140717 A1 | 9/2016 |
| WO | WO-2018068691 A1 | 4/2018 |

OTHER PUBLICATIONS

Wikipedia contributors. (Jul. 4, 2023). G418. Wikipedia. https://en.wikipedia.org/wiki/G418 (Year: 2023).*
C. Sherer, et. al "Heterocyclic scaffolds as promising anticancer agents against tumours of the central nervous system: Exploring the scope of indole and carbazole derivatives" summarizes the state of the art (European Journal of Medicinal Chemistry, 97, 2015, 552-560) (Year: 2015).*

(Continued)

*Primary Examiner* — Clinton A Brooks
*Assistant Examiner* — Josmalen M. Ramos-Lewis
(74) *Attorney, Agent, or Firm* — Foley Hoag LLP; Dana M. Gordon; Benjamin A. Vaughan

(57) ABSTRACT

Disclosed are a new indoline-1-carboxamide compound for regulating or inhibiting the activity of vascular endothelial growth factor receptor (VEGFR), a preparation method therefor, and the medical use thereof. Specifically, the present invention relates to a compound of general formula (I) or a pharmaceutically acceptable salt thereof, a pharmaceutical composition comprising the compound or a pharmaceutically acceptable salt thereof, a method for treating and/or preventing VEGFR-mediated related disorders, especially tumors, using the compound or a pharmaceutically acceptable salt thereof, as well as a method for preparing the compound or a pharmaceutically acceptable salt thereof. The present invention also relates to the use of the compound or a pharmaceutically acceptable salt thereof or the pharmaceutical composition comprising the compound or a pharmaceutically acceptable salt thereof in the manufacture of a medicament for treating and/or preventing VEGFR-mediated related disorders, especially tumors. Each substituent of general formula (I) has the same definition as that in the specification.

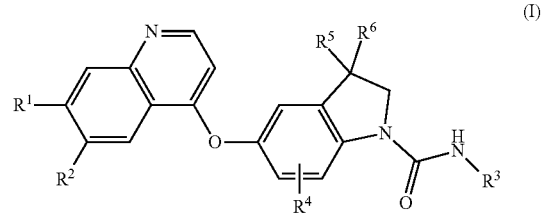

6 Claims, No Drawings

(56) References Cited

OTHER PUBLICATIONS

First Chinese Office Action for CN Application No. 201980031818.0 dated May 7, 2022 w/ English Translation.
Extended European Search Report for EP Application No. 19804493 dated Jan. 21, 2022.
"Eisai Presents Results of Phase Ib/II Clinical Study of Lenvima (Lenvatinib) in Combination With Pembrolizumab for Renal Cell Carcinoma in Oral Session at ESMO 2017 Congress," Abstract No. 8470 (2017).
"Further Study of Combination of Eisai's Lenvatinib And Merck's Pembrolizumab In Previously Treated Patients With Metastatic Endometrial Cancer Supported By Interim Analysis of Ongoing Phase 1B/2 Trial," 2017 ASCO Annual Meeting.

* cited by examiner

INDOLINE-1-FORMAMIDE COMPOUND, PREPARATION METHOD THEREFOR, AND MEDICAL USE THEREOF

FIELD OF THE INVENTION

The present invention relates to a new indoline-1-carboxamide compound or a pharmaceutically acceptable salt thereof for regulating or inhibiting the activity of vascular endothelial cell growth factor receptor (VEGFR), a pharmaceutical composition comprising the compound or a pharmaceutically acceptable salt thereof, the preparation method of the compound or a pharmaceutically acceptable salt thereof, and use of the compound or a pharmaceutically acceptable salt thereof or the pharmaceutical composition comprising the compound or a pharmaceutically acceptable salt thereof in the manufacture of a medicament for treating and/or preventing VEGFR-mediated related disorders, especially tumors, as well as method of using the same.

BACKGROUND OF THE INVENTION

Angiogenesis is a complicated physiological process that is stimulated and regulated by a variety of factors, including vascular endothelial growth factor (VEGF), fibroblast growth factor (FGF), platelet-derived growth factor (PDGF), angiopoietin, interleukin 6 (IL-6), etc. through different signaling pathways, and plays an important role in tumor growth and metastasis. For example, VEGF binds to its receptor VEGFR1/2/3 to trigger a downstream signaling cascade to promote endothelial cell proliferation, survival, migration, and vascular permeability. VEGFR1 (FLT1 receptor) and VEGFR2 (KDR/FLK1) are mainly related to angiogenesis, while VEGFR3 (FLT4 receptor) is mainly related to lymphangiogenesis. VEGFR2 is universally expressed in almost all types of endothelial cells, while the expression of VEGFR1/3 is restricted to specific vascular support tissues.

VEGFR is expressed at a low level in normal human tissues, but is highly expressed in most tumors. VEGFR is not only expressed in vascular endothelial cells, but also in tumor cells. It not only promotes the division and proliferation of vascular endothelial cells, but also induces tumor angiogenesis and promotes the growth and metastasis of tumor cells. Therefore, by inhibiting the activity of VEGFR and blocking its signal transduction, tumor angiogenesis can be prevented, thereby inhibiting tumor growth and metastasis and controlling tumor growth. Hence, VEGFR is an important anti-tumor target. Several small molecule VEGFR inhibitors are commercially available, such as sorafenib, sunitinib, lenvatinib, axitinib, and cabozantinib; some are undergoing clinical research, such as fruquintinib, cediranib and lucitanib. Most of them are multi-kinase inhibitors with different clinical efficacies and toxic side effects, providing alternative treatment means for patients suffering from tumors.

Current immune checkpoint inhibitors such as PD-1/PD-L1 have shown good clinical effects on a variety of tumors, but the response rate needs to be further improved. Whether the combination of PD-1/PD-L1 with inhibitors of kinases like VEGFR can produce a synergistic effect to improve the efficacy has attracted the attention of many biopharmaceutical companies (WO2015088847, WO2016140717, WO2018068691, etc.), and clinical trials of a variety of drug combinations have been launched. The clinical Ib/II results of PD-1 and lenvatinib show that the combination therapy is superior to single-agent therapy, and has achieved a higher response rate in the treatment of metastatic renal cell carcinoma (ESMO 2017 Congress, Abstract No. 8470) and endometrial cancer (2017 ASCO).

Based on the prospects shown by VEGFR inhibitors in the treatment of multiple tumors alone and in combination with immunotherapy, the present invention designed and synthesized novel compounds of general formula (I), and found that compounds with such structures exhibit excellent effect in inhibiting activity of VEGFR.

SUMMARY OF THE INVENTION

The present invention provides a compound represented by general formula (I) as a VEGFR inhibitor:

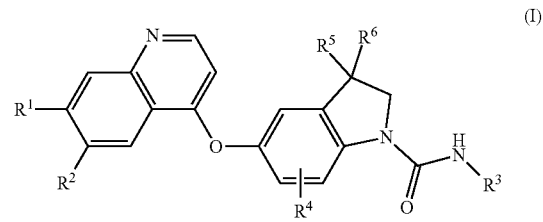

or a pharmaceutically acceptable salt, prodrug, stable isotope derivative, isomer thereof and mixture thereof, wherein:

$R^1$ is $—OR^7$;

$R^2$ is independently selected from $—OR^8$ or $—C(O)NHR^8$;

$R^3$ is optionally substituted $C_{1-4}$ alkyl, $C_{3-7}$ cycloalkyl, 4-7 membered heterocyclyl, phenyl, 5-6 membered heteroaryl;

$R^4$ is independently selected from H, halogen, CN, $C_{1-4}$ alkyl;

$R^5$ and $R^6$ are each independently selected from H, halogen, $C_{1-4}$ alkyl, $—OR^7$; or $R^5$ and $R^6$, together with the carbon atom attached, form a 3-7 membered ring optionally containing heteroatom(s) selected from O, N and S;

$R^7$ and $R^8$ are each independently selected from H or optionally substituted $C_{1-4}$ alkyl;

the optional substitution refers to substitution by a substituent selected from the group consisting of halogen, $—CN$, $—NO_2$, oxo, $—SF_5$, $C_{1-4}$ alkyl, $C_{3-7}$ cycloalkyl, 4-7 membered heterocyclic group, phenyl, 5-6 membered heteroaryl, $—OR'$, $—NR'R''$, $—C(O)R'$, $—C(O)OR'$, $—C(O)NR'R''$, $—C(O)N(R')OR''$, $—OC(O)R'$, $—OC(O)NR'R''$, $—N(R')C(O)OR''$, $—N(R')C(O)R''$, $—N(R''')C(O)NR'R''$, $—N(R')S(O)_2R''$, $—S(O)_mR'$, $—S(O)_2NR'R''$, wherein R', R'' and R''' are each independently selected from H, $C_{1-4}$ alkyl, $C_{3-7}$ cycloalkyl, halogenated $C_{1-4}$ alkyl, 4-7 membered heterocyclyl, $C_{6-10}$ aryl, 5-10 membered heteroaryl; R' and R'' on the same nitrogen atom optionally together with the nitrogen atom to which they are attached form a 4-7 membered heterocyclic ring optionally containing additional heteroatom(s) selected from O, S and N; and m is 1 or 2.

One embodiment of the present invention relates to a compound represented by the above general formula (I) or a pharmaceutically acceptable salt, prodrug, stable isotope derivative, isomer thereof and mixture thereof, wherein $R^2$ is independently selected from —OC$_{1-4}$ alkyl, —C(O)NH$_2$ or —C(O)NH—C$_{1-4}$ alkyl, preferably R$^2$ is —OCH$_3$, more preferably R$^2$ is —C(O)NH$_2$.

One embodiment of the present invention relates to a compound represented by the above general formula (I) or a pharmaceutically acceptable salt, prodrug, stable isotope derivative, isomer thereof and mixture thereof, wherein R$^7$ is optionally substituted C$_{1-4}$ alkyl, preferably R$^7$ is C$_{1-4}$ alkyl, more preferably R$^7$ is CH$_3$.

Another embodiment of the present invention relates to a compound according to any one of the above embodiments or a pharmaceutically acceptable salt, prodrug, stable isotope derivative, isomer thereof and mixture thereof, wherein R$^4$ is H or F, preferably R$^4$ is H.

Another embodiment of the present invention relates to a compound according to any one of the above embodiments or a pharmaceutically acceptable salt, prodrug, stable isotope derivative, isomer thereof and mixture thereof, wherein R$^5$ and R$^6$ are each independently selected from H or F, preferably R$^5$ and R$^6$ are H.

One embodiment of the present invention relates to a compound represented by the above general formula (I), wherein the compound is selected from but not limited to:

| Compound No. | Structure and name of compound |
|---|---|
| 1. | 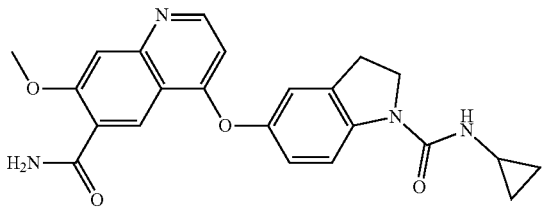 [SMILES: COc1cc2nccc(Oc3ccc4c(c3)CCN4C(=O)NC3CC3)c2cc1C(N)=O]<br>4-((1-(cyclopropylcarbamoyl)indolin-5-yl)oxy)-7-methoxyquinoline-6-carboxamide |
| 2. | 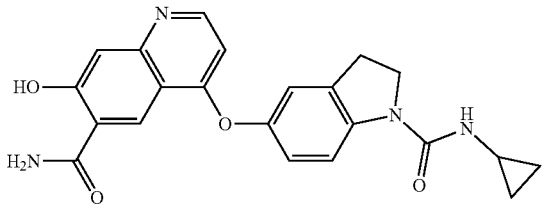 [SMILES: NC(=O)c1cc2c(Oc3ccc4c(c3)CCN4C(=O)NC3CC3)ccnc2cc1O]<br>4-((1-(cyclopropylcarbamoyl)indolin-5-yl)oxy)-7-hydroxyquinoline-6-carboxamide |
| 3. | 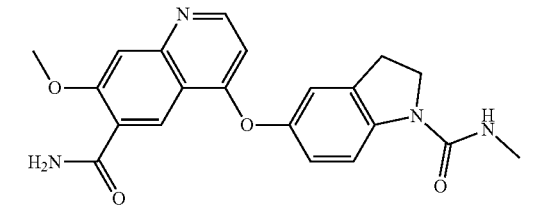<br>7-methoxy-4-((1-(methylcarbamoyl)indolin-5-yl)oxy)quinoline-6-carboxamide |
| 4. | 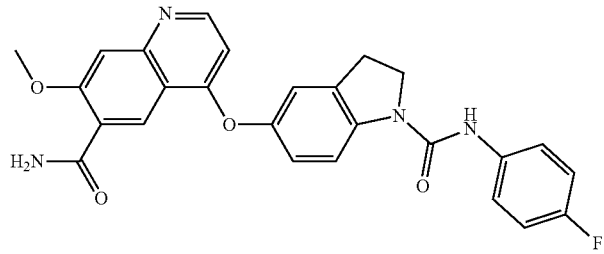 [SMILES: COc1cc2nccc(Oc3ccc4c(c3)CCN4C(=O)Nc3ccc(F)cc3)c2cc1C(N)=O]<br>4-((1-((4-fluorophenyl)carbamoyl)indolin-5-yl)oxy)-7-methoxyquinoline-6-carboxamide |

-continued

| Compound No. | Structure and name of compound |
|---|---|
| 5. | 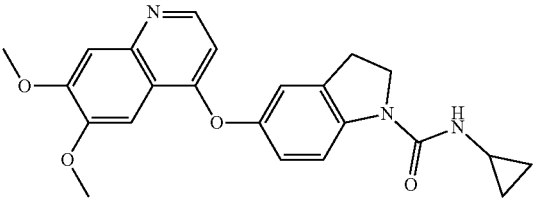 [SMILES: COc1cc2nccc(Oc3ccc4c(c3)CCN4C(=O)NC3CC3)c2cc1OC]<br>N-cyclopropyl-5-((6,7-dimethoxyquinolin-4-yl)oxy)indoline-1-carboxamide |
| 6. | 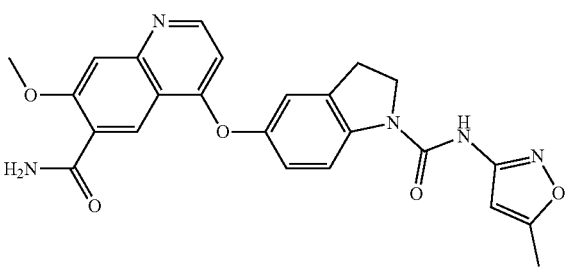 [SMILES: COc1cc2nccc(Oc3ccc4c(c3)CCN4C(=O)Nc3cc(C)on3)c2cc1C(N)=O]<br>7-methoxy-4-((1-((5-methylisoxazol-3-yl)carbamoyl)indolin-5-yl)oxy)quinoline-6-carboxamide | or a pharmaceutically acceptable salt, prodrug, stable isotope derivative, isomer thereof and mixture thereof.

The compounds of the present invention have significant inhibitory effect on the enzyme activity of VEGFR2, preferably have an $IC_{50}$ of less than 100 nM, and more preferably have an $IC_{50}$ of less than 10 nM.

Another aspect of the present invention relates to a compound represented by the general formula (I) or a pharmaceutically acceptable salt, prodrug, stable isotope derivative, isomer thereof and mixture thereof for use as a medicament or for medical use, which is used for treating or preventing VEGFR-mediated related diseases, especially tumors, including but not limited to melanoma, lymphoma, thyroid cancer, kidney cancer, liver cancer, prostate cancer, colon cancer, rectal cancer, stomach cancer, brain cancer, bladder cancer, ovarian cancer, head and neck cancer, breast cancer, lung cancer, glioma, etc. Therefore, in another aspect, the present invention provides a method for treating or preventing VEGFR-mediated diseases (such as said tumors), which comprises administering to a patient in need thereof a therapeutically effective amount of a compound of the present invention or a pharmaceutically acceptable salt, prodrug, stable isotope derivative, isomer thereof and mixture thereof, or a pharmaceutical composition comprising the compound.

The present invention further relates to a pharmaceutical composition comprising a compound of the present invention or a pharmaceutically acceptable salt, prodrug, stable isotope derivative, isomer thereof and mixture thereof, and a pharmaceutically acceptable carrier and excipient.

Another aspect of the present invention relates to use of a compound represented by the general formula (I) or a pharmaceutically acceptable salt, prodrug, stable isotope derivative, isomer thereof and mixture thereof, or the pharmaceutical composition in the manufacture of a medicament for treating or preventing VEGFR-mediated diseases, such as tumors.

Another aspect of the present invention relates to a pharmaceutical composition comprising a compound represented by the general formula (I) or a pharmaceutically acceptable salt, prodrug, stable isotope derivative, isomer thereof and mixture thereof, and at least one additional drug, wherein the at least one additional drug is a chemotherapeutic agent or an immunomodulator (such as an immune checkpoint inhibitor).

According to the present invention, the medicament can be in any pharmaceutical dosage form, including but not limited to tablets, capsules, solutions, freeze-dried preparations, and injections.

The pharmaceutical formulation of the present invention can be administered in the form of a dosage unit containing a predetermined amount of active ingredient per dosage unit. Such a unit may contain, for example, 0.5 mg to 1 g, preferably 1 mg to 700 mg, particularly preferably 5 mg to 300 mg of the compound of the present invention, depending on the disorders to be treated, the administration method, and the age, weight and condition of the patient. Preferred dosage unit formulations are those containing the active ingredient in daily or divided doses or corresponding fractions thereof as indicated above. In addition, such pharmaceutical formulations can be prepared using the methods known in the pharmaceutical field.

The pharmaceutical formulation of the present invention may be suitable for administration by any desired suitable method, for example by oral (including buccal or sublingual), rectal, nasal, topical (including buccal, sublingual or transdermal), vaginal or parenteral (including subcutaneous, intramuscular, intravenous or intradermal) administration. Such formulations may be prepared using all methods known in the pharmaceutical field by for example combining the active ingredient with one or more excipients or one or more adjuvants.

DETAILED DESCRIPTION OF THE INVENTION

Unless stated to the contrary, the following terms used in the specification and claims have the following meanings.

The expression "$C_{x-y}$" used herein refers to the range of the number of carbon atoms, where x and y are both integers. For example, $C_{3-8}$ cycloalkyl means a cycloalkyl group having 3-8 carbon atoms, that is, a cycloalkyl group having 3, 4, 5, 6, 7 or 8 carbon atoms. It is to be understood that "$C_{3-8}$" also includes any sub-range therein, such as $C_{3-7}$, $C_{3-6}$, $C_{4-7}$, $C_{4-6}$, $C_{5-6}$, and the like.

"Alkyl" refers to a saturated linear or branched hydrocarbon group containing 1 to 20 carbon atoms, for example 1 to 8 carbon atoms, 1 to 6 carbon atoms, or 1 to 4 carbon atoms. Non-limiting examples of alkyl group include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl and 2-ethylbutyl. The alkyl group may be optionally substituted.

"Cycloalkyl" refers to a saturated cyclic hydrocarbyl substituent containing 3 to 14 carbon ring atoms. The cycloalkyl group may be a single carbon ring, usually containing 3 to 8, 3 to 7, or 3 to 6 carbon ring atoms. Non-limiting examples of monocyclic cycloalkyl group include cyclopropyl, cyclobutyl, cyclopentyl, cyclohexyl, and cycloheptyl. Cycloalkyl group can alternatively be bicyclic or tricyclic rings fused together, such as decalinyl. The cycloalkyl group may be optionally substituted.

"Heterocyclic group/heterocyclyl or heterocyclic ring" refers to a saturated or partially unsaturated monocyclic or polycyclic cyclic group, which includes 3 to 20 ring atoms, for example, 3 to 14, 3 to 12, 3 to 10, 3 to 8, 3 to 6, or 5 to 6 ring atoms, of which one or more ring atoms are selected from nitrogen, oxygen or S(O). (where m is an integer of 0 to 2), but not including the ring part of —O—O—, —O—S— or —S—S—, and the remaining ring atoms are carbon. It preferably includes 3 to 12 ring atoms, more preferably 3 to 10 ring atoms, more preferably 4 to 7 ring atoms, most preferably 5 or 6 ring atoms, of which 1 to 4 are heteroatom(s), more preferably 1 to 3 are heteroatom(s), and most preferably 1 to 2 are heteroatom(s). Non-limiting examples of monocyclic heterocyclic group include pyrrolidinyl, piperidinyl, piperazinyl, pyranyl, morpholinyl, thiomorpholinyl, homopiperazinyl, oxacyclohexyl and azetidinyl. Polycyclic heterocyclic groups include fused, bridged or spiro polycyclic heterocyclic groups, such as octahydrocyclopenta[c]pyrrole, octahydropyrrolo[1,2-a]pyrazine, 3,8-diazabicyclo[3.2.1]octane, 5-azaspiro[2.4]heptane, 2-oxa-7-azaspiro[3.5]nonane. The heterocyclic group or heterocyclic ring may be optionally substituted.

"Aryl or aromatic ring" refers to an aromatic monocyclic or fused polycyclic group containing 6 to 14 carbon atoms, preferably 6 to 10 membered, such as phenyl and naphthyl, and most preferably phenyl. The aryl ring may be fused to a heteroaryl, heterocyclic or cycloalkyl ring, wherein the ring connected to the parent structure is an aryl ring. Non-limiting examples include:

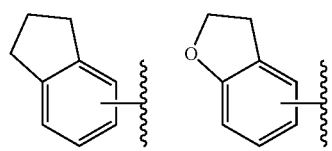

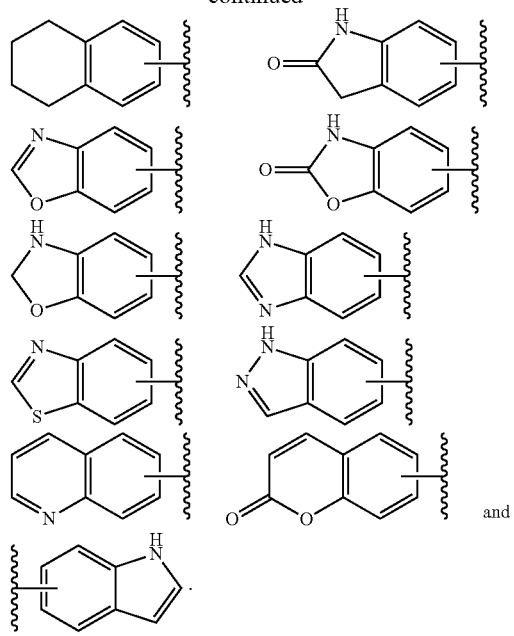

The aryl group or aromatic ring may be optionally substituted.

"Heteroaryl or heteroaromatic ring" refers to a heteroaromatic system containing 5 to 14 ring atoms, where 1 to 4 ring atoms are selected from heteroatoms including oxygen, sulfur and nitrogen. The heteroaryl group is preferably 5 to 10 membered. More preferably, the heteroaryl group is 5-membered or 6-membered, such as furyl, thienyl, pyridyl, pyrrolyl, N-alkylpyrrolyl, pyrimidinyl, pyrazinyl, pyrazolyl, imidazolyl, tetrazolyl, oxazolyl, isoxazolyl, thiazolyl, isothiazolyl, quinolinyl and the like. The heteroaryl ring may be fused to an aryl, heterocyclyl or cycloalkyl ring, wherein the ring connected to the parent structure is a heteroaryl ring. Non-limiting examples include:

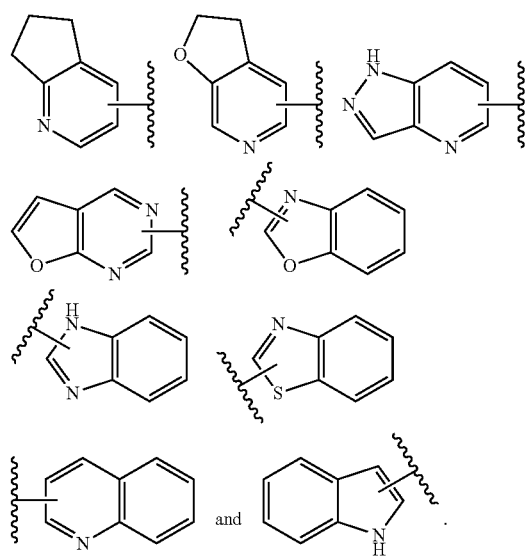

The heteroaryl or heteroaromatic ring may be optionally substituted.

"Halogen" refers to fluorine, chlorine, bromine or iodine.

"Cyano" refers to —CN.

"Optional" or "optionally" implies that the subsequently described event or environment may, but not necessarily, occur, including the to occurrence or non-occurrence of the event or environment. For example, "heterocyclic group optionally substituted with an alkyl group" implies that an alkyl group may be, but not be necessarily present, and the expression includes the case where the heterocyclic group is substituted with an alkyl group and the case where the heterocyclic group is not substituted with an alkyl group.

"Optionally substituted" refers to one or more hydrogen atoms in the group, preferably 5, and more preferably 1 to 3 hydrogen atoms are independently substituted by a corresponding number of substituents. It goes without saying that the substituents are only in their possible chemical positions, and those skilled in the art can determine (through experiment or theory) possible or impossible substitutions without too much effort. For example, an amino group or a hydroxyl group with free hydrogen may be unstable when bonded with a carbon atom having an unsaturated (eg, olefinic) bond. The substituents include but are not limited to halogen, —CN, —NO$_2$, oxo, —SF$_5$, C$_{1-4}$ alkyl, C$_{3-7}$ cycloalkyl, 4-7 membered heterocyclyl, phenyl, 5-6 membered heteroaryl, —OR', —NR'R'', —C(O)R', —C(O)OR', —C(O)NR'R'', —C(O)N(R')OR'', —OC(O)R', —OC(O)NR'R'', —N(R')C(O)OR'', —N(R')C(O)R'', —N(R''')C(O)NR'R'', —N(R')S(O)$_2$R'', —S(O)$_m$R' (m is 1 or 2), —S(O)$_2$NR'R'', etc., wherein R', R'' and R''' are each independently selected from H, C$_{1-4}$ alkyl, C$_{3-7}$ cycloalkyl, halogenated C$_{1-4}$ alkyl, 4-7 membered heterocyclyl, C$_{6-10}$ aryl, 5-10 membered heteroaryl, etc.; R' and R'' on the same nitrogen atom optionally together with the nitrogen atom to which they are attached form a 4-7 membered heterocycle optionally containing further heteroatom(s) selected from O, S and N.

"Isomers" refer to compounds that have the same molecular formula but differ in the nature or sequence of bonding of their atoms or the arrangement of their atoms in space. Isomers that differ in the arrangement of their atoms in space are called "stereoisomers". Stereoisomers include optical isomers, geometric isomers and conformational isomers.

The compounds of the present invention may exist in the form of optical isomers. These optical isomers are of the "R" or "S" configuration depending on the configuration of the sub stituents around the chiral carbon atom. Optical isomers include enantiomers and diastereomers. Methods for preparing and isolating optical isomers are known in the art.

The compounds of the present invention may also exist in geometric isomers. The present invention contemplates various geometric isomers and mixtures thereof resulting from the distribution of substituents around carbon-carbon double bonds, carbon-nitrogen double bonds, cycloalkyl or heterocyclic groups. Substituents around a carbon-carbon double bond or carbon-nitrogen bond are designated as Z or E configuration, and substituents around a cycloalkyl or heterocyclic ring are designated as cis or trans configuration.

The compounds of the present invention may also exhibit tautomerism, such as keto-enol tautomerism.

It is to be understood that the invention includes any tautomeric or stereoisomeric forms and mixtures thereof and is not limited to any one of the tautomeric or stereoisomeric forms used in the nomenclature or chemical structural formula of the compound.

"Isotopes" includes all isotopes of atoms occurring in the compounds of the present invention. Isotopes include those atoms that have the same atomic number but different mass numbers. Examples of isotopes suitable for incorporation into the compounds of the present invention are hydrogen, carbon, nitrogen, oxygen, phosphorus, fluorine and chlorine, for example but not limited to $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl. Isotopically labeled compounds of the invention can generally be prepared by conventional techniques known to those skilled in the art or by methods similar to those described in the accompanying examples, using suitable isotopically labeled reagents in place of non-isotopically labeled reagents. Such compounds have a variety of potential uses, for example, as a standard and reagent in the determination of biological activity. In the case of stable isotopes, such compounds have the potential to advantageously alter biological, pharmacological or pharmacokinetic properties.

"Prodrugs" means that the compounds of the invention may be administered in the form of a prodrug. Prodrugs are derivatives which are converted to the biologically active compounds of the invention under physiological conditions in vivo, for example, by oxidation, reduction, hydrolysis, etc. (each of which is carried out using an enzyme or without the participation of an enzyme). Examples of prodrugs are compounds wherein the amino group in the compounds of the invention is acylated, alkylated or phosphorylated, such as eicosanoylamino, alanylamino, pivaloyloxymethylamino, or wherein the hydroxy group is acylated, alkylated, phosphorylated or converted to borate, such as acetoxy, palmitoyloxy, pivaloyloxy, succinyloxy, fumaryloxy, alanyloxy, or wherein the carboxyl group is esterified or amidated, or wherein a thiol group forms a disulfide bridge with a carrier molecule, such as a peptide, that selectively delivers the drug to the target and/or to the cytosol of the cell. These compounds can be prepared from the compounds of the present invention according to known methods.

"Pharmaceutically acceptable salt" refers to a salt made of a pharmaceutically acceptable base or acid, including an inorganic base or acid, and an organic base or acid. Where the compounds of the invention contain one or more acidic or basic groups, the invention also includes their corresponding pharmaceutically acceptable salts. Thus, the compound of the invention containing an acidic group may be present in the form of a salt and may be used according to the invention, for example as an alkali metal salt, an alkaline earth metal salt or as an ammonium salt. More specific examples of such salts include sodium, potassium, calcium, magnesium salts or salts with ammonia or organic amines such as ethylamine, ethanolamine, triethanolamine or amino acids. The compound of the invention containing a basic group may be present in the form of a salt and may be used in the form of their addition salts with inorganic or organic acids according to the invention. Examples of suitable acids include hydrochloric acid, hydrobromic acid, phosphoric acid, sulfuric acid, nitric acid, methanesulfonic acid, p-toluenesulfonic acid, naphthalenedisulfonic acid, oxalic acid, acetic acid, tartaric acid, lactic acid, salicylic acid, benzoic acid, formic acid, propionic acid, pivalic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to those skilled in the art. If the compound of the present invention contains both acidic and basic groups in the molecule, the present invention includes an internal salt or a betaine in addition to the salt forms mentioned. Each salt can be obtained by conventional methods known to those skilled in the art, for example, by contacting an organic or inorganic acid or base in a solvent or dispersant, or by anion exchange or cation exchange with other salts.

"Pharmaceutical composition" refers to a composition comprising one or more compounds described herein or a pharmaceutically acceptable salt, prodrug, stable isotope derivative, isomer thereof and mixtures thereof, and other components such as pharmaceutically acceptable carriers and excipients. The pharmaceutical composition intends to promote the administration to the organism and facilitate the absorption of the active ingredient, so as to exert biological activity.

Therefore, when referring to "compounds", "compounds of the present invention" or "compounds according to the present invention" in this application, all forms of the compounds are included, such as pharmaceutically acceptable salts, prodrugs, stable isotope derivatives, isomers thereof and mixtures thereof.

As used herein, the term "tumor" includes benign tumors and malignant tumors (such as cancer).

As used herein, the term "therapeutically effective amount" refers to the amount of the compound of the present invention that can effectively inhibit the function of VEGFR and/or treat or prevent the disease.

Synthetic Methods

The present invention also provides a method for preparing the compound. The compounds of the general formula (I) of the present invention can be prepared by the following exemplary methods and examples, but the methods and examples should not be construed as being limiting the scope of the invention in any ways. The compounds of the invention may also be synthesized by synthetic techniques known to those skilled in the art, or a combination of methods known in the art and methods of the invention may be employed. The product produced in each step of the reaction is obtained by separation techniques known in the art including, but not limited to, extraction, filtration, distillation, crystallization, chromatographic separation, etc. The starting materials and chemical reagents required for the synthesis can be conventionally synthesized according to the literature (available on SciFinder) or be purchased.

The indoline-1-carboxamide compounds of the general formula (I) of the present invention can be synthesized according to the route described in method A: Urea A2 is produced from indoline A1 via conventional condensation methods for example by using N,N'-carbonyldiimidazole (CDI) condensing agent, reacting with isocyanate, first forming phenylindoline-1-carboxylate and then reacting with amine, etc.; A2 is hydrogenated and debenzylated to obtain A3; A3 is subjected to substitution reaction with 4-chloroquinoline under base catalysis to produce the target product A4.

Method A:

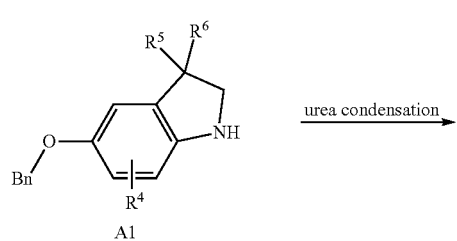

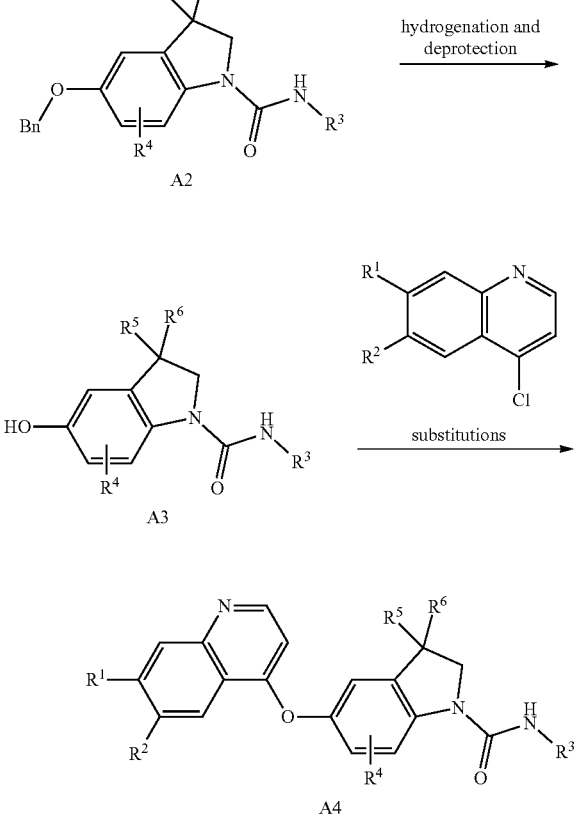

The indoline-1-carboxamide compounds of the general formula (I) of the present invention can also be synthesized according to the route described in method B: N-Boc protected indoline B1 is subjected to substitution reaction with 4-chloroquinoline under base catalysis to produce B2; Removal of Boc from B2 with acid yields B3; B3 is then subjected to urea condensation to produce target product A4.

Method B:

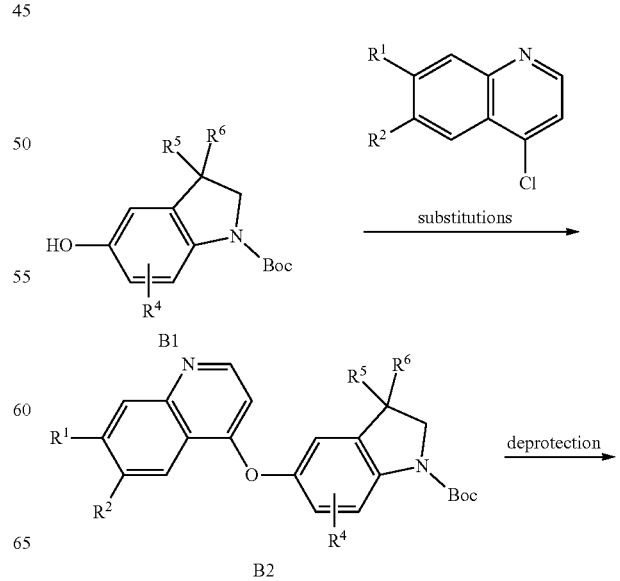

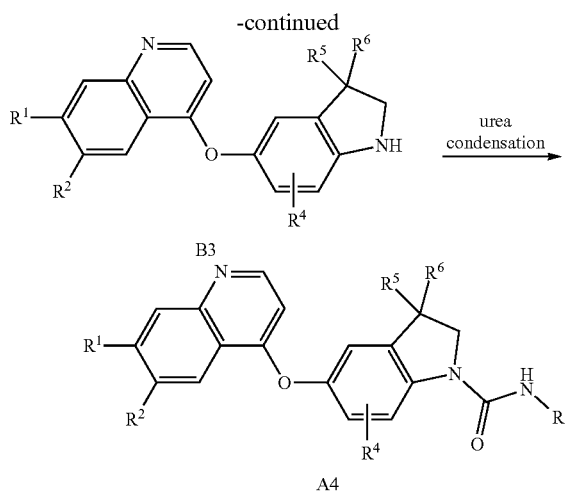

EXAMPLES

The structure of the compound was determined by nuclear magnetic resonance (NMR) or mass spectrometry (MS). NMR was measured by Bruker ASCEND-400 NMR spectrometer, the solvent for determination was deuterated dimethyl sulfoxide (DMSO-$d_6$), deuterated chloroform ($CDCl_3$) or deuterated methanol ($CD_3OD$), the internal standard was tetramethylsilane (TMS), and chemical shifts were given in units of $10^{-6}$ (ppm).

MS was measured using an Agilent SQD (ESI) mass spectrometer (manufacturer: Agilent, model: 6120).

HPLC was run by using an Agilent 1260 DAD high pressure liquid chromatograph (Poroshell 120 EC-C18, 50×3.0 mm, 2.7 μm column) or a Waters Arc high pressure liquid chromatograph (Sunfire C18, 150×4.6 mm, 5 μm column).

Qingdao Ocean GF254 silica gel plate was used as thin-layer chromatography silica gel plate. The specification of silica gel plate used for thin-layer chromatography (TLC) was 0.15 mm~0.2 mm. The specification for thin layer chromatography separation and purification was 0.4 mm~0.5 mm.

Generally, Qingdao Ocean 200~300 mesh silica gel was used as carrier for column chromatography.

The known starting materials of the present invention can be synthesized according to methods known in the art, or can be purchased from ABCR GmbH & Co. KG, Acros Organics, Aldrich Chemical Company, Accela ChemBio Inc., Beijing Ouhe Technology Co., etc.

Unless otherwise specified, the reactions were carried out under an argon or nitrogen atmosphere.

An argon or nitrogen atmosphere means that the reaction flask is connected to an argon or nitrogen balloon of about 1 L volume.

A hydrogen atmosphere means that the reaction bottle is connected to a hydrogen balloon of about 1 L volume.

The hydrogenation reaction is usually evacuated, filled with hydrogen, which is repeated for three times.

CEM Discover-SP microwave reactor was used for microwave reaction.

Unless otherwise specified in the examples, the reaction temperature was room temperature, and the temperature range was 20° C.-30° C.

The reaction progress in the examples was monitored by an Agilent liquid chromatograph/mass spectrometer (1260/ 6120). The reaction progress also can be monitored by thin layer chromatography (TLC), and the developing solvent system used was: A: dichloromethane and methanol system; B: petroleum ether and ethyl acetate system, and the volume ratio of the solvents was adjusted based on the polarity of the compound.

The eluent system used for purifying the compound by column chromatography and the developing solvent system for the thin layer chromatography included: A: dichloromethane and methanol systems; B: petroleum ether and ethyl acetate system, and the volume ratio of the solvents was adjusted based on the polarity of the compound. It could also be adjusted by adding a small amount of triethylamine and acidic or alkaline reagents, or using other solvent systems. The compound was also purified using Waters mass spectrometry guided automatic preparation system (mass detector: SQD2), and the reversed-phase high pressure column (XBridge-C18, 19×150 mm, 5 μm) was eluted with appropriate acetonitrile/water (containing 0.1% trifluoroacetic acid or formic acid) or acetonitrile/water (containing 0.05% ammonia) gradient at a flow rate of 20 mL/min according to the polarity of the compound.

Examples 1 and 2

4-((1-(Cyclopropylcarbamoyl)indolin-5-yl)oxy)-7-methoxyquinoline-6-carboxamide 1

4-((1-(Cyclopropylcarbamoyl)indolin-5-yl)oxy)-7-hydroxyquinoline-6-carboxamide 2

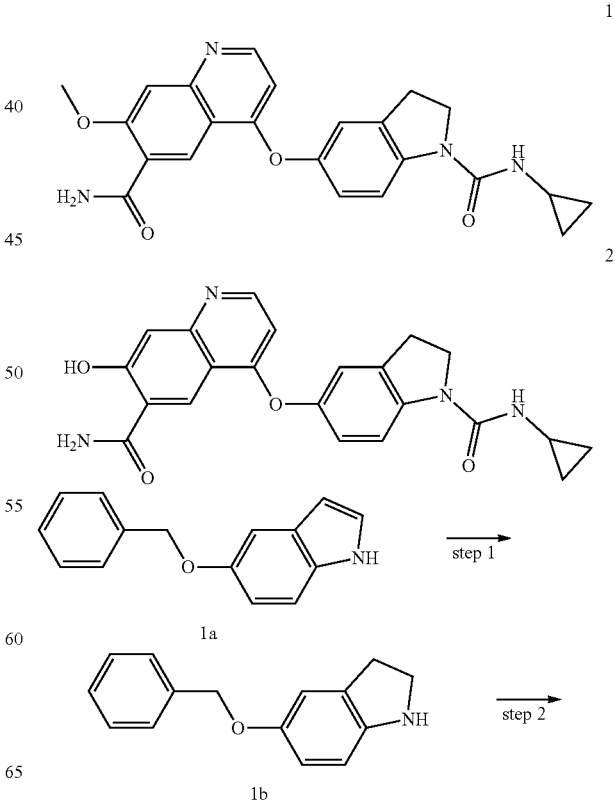

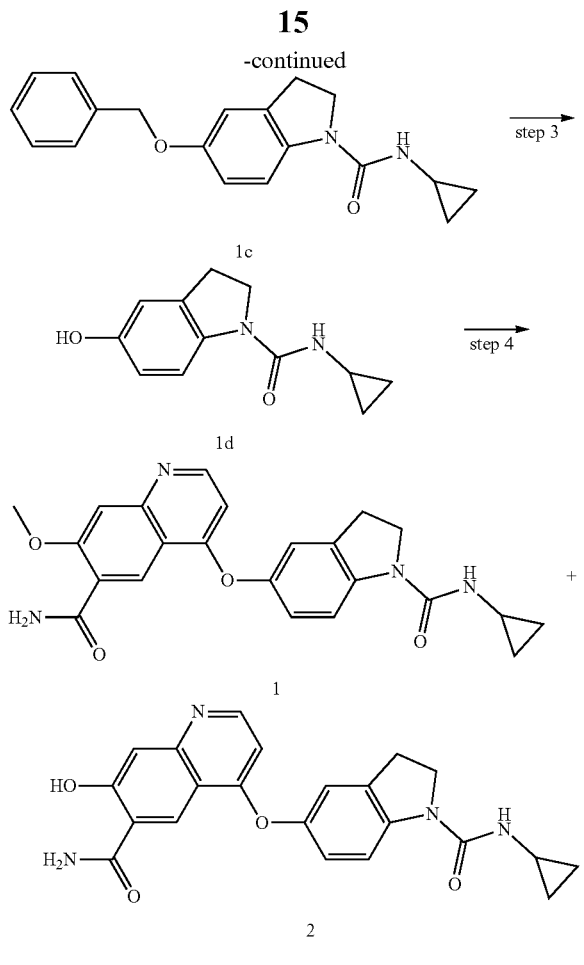

Step 1

5-(Benzyloxy)indoline

Compound 5-(benzyloxy)indole 1a (1.06 g, 4.75 mmol) was dissolved in acetic acid (10 mL), and then sodium cyanoborohydride (447 mg, 7.12 mmol) was added. After stirring for 1 hour at room temperature, the mixture was adjusted to pH=8 with IN lithium hydroxide solution, and then extracted with ethyl acetate (50 mL×3). The organic phases were combined and dried over anhydrous sodium sulfate. After filtration, the solvent was removed from the filtrate under reduced pressure. The residue was purified by silica gel column chromatography (dichloromethane/methanol=20/1) to obtain the target product 5-(benzyloxy)indoline 1b (883 mg, yellow oil), yield: 88%.

MS m/z (ESI): 226[M+1]

$^1$H NMR (400 MHz, CDCl$_3$) δ 7.45-7.28 (m, 5H), 6.85-6.81 (m, 1H), 6.68 (dd, J=8.4, 2.5 Hz, 1H), 6.63 (d, J=8.4 Hz, 1H), 4.99 (s, 2H), 3.56 (t, J=8.3 Hz, 2H), 3.01 (t, J=8.3 Hz, 2H).

Step 2

5-(Benzyloxy)-N-cyclopropylindoline-1-carboxamide

Cyclopropylamine (46 mg, 0.8 mmol) was dissolved in N,N-dimethylformamide (2 mL), then N,N'-carbonyldiimidazole (156 mg, 0.96 mmol) was added, and the mixture was then heated to 65° C. and stirred for 2 hours. After cooling to room temperature, 5-(benzyloxy)indoline 1b (113 mg, 0.5 mmol) was added, and then the temperature was raised to 65° C. again and stirred for 2 hours. After cooling to room temperature, the mixture was quenched with water, and then extracted with ethyl acetate (20 mL×3). The organic phases were combined and washed with water (20 mL×2) and saturated brine (20 mL) successively, and then dried over anhydrous sodium sulfate. After filtration, the solvent was removed from the filtrate under reduced pressure, and the residue was purified by silica gel column chromatography (petroleum ether/ethyl acetate=1/1 to 1/2) to obtain the target product 5-(benzyloxy)-N-cyclopropylindoline-1-carboxamide 1c (124 mg, white solid), yield: 80%.

MS m/z (ESI): 309[M+1]

$^1$H NMR (400 MHz, CDCl$_3$) δ 7.79 (d, J=8.5 Hz, 1H), 7.45-7.28 (m, 5H), 6.82-6.74 (m, 2H), 5.01 (s, 2H), 4.75 (s, 1H), 3.83 (t, J=8.6 Hz, 2H), 3.11 (t, J=8.5 Hz, 2H), 2.72 (tt, J=7.0, 3.7 Hz, 1H), 0.81-0.75 (m, 2H), 0.57-0.51 (m, 2H).

Step 3

N-Cyclopropyl-5-hydroxyindoline-1-carboxamide

Compound 5-(benzyloxy)-N-cyclopropylindoline-1-carboxamide 1c (530 mg, 1.72 mmol) was dissolved in methanol (30 mL), and then 10% palladium on carbon (110 mg) was added. The mixture was stirred under a hydrogen atmosphere at room temperature for 2 hours. The reaction was filtered after it completed, and the solvent was removed from the filtrate under reduced pressure to obtain the target product N-cyclopropyl-5-hydroxyindoline-1-carboxamide 1d (308 mg, white solid), yield: 82%.

MS m/z (ESI): 219[M+1]

Step 4

4-((1-(Cyclopropylcarbamoyl)indolin-5-yl)oxy)-7-methoxyquinoline-6-carboxamide and 4-((1-(cyclopropylcarbamoyl)indolin-5-yl)oxy)-7-hydroxyquinoline-6-carboxamide Compound N-cyclopropyl-5-hydroxyindoline-1-carboxamide 1d (110 mg, 0.5 mmol), 4-chloro-7-methoxyquinoline-6-carboxamide (118 mg, 0.5 mmol), diisopropylethylamine (97 mg, 0.75 mmol) and N-methylpyrrolidinone (0.2 mL) were mixed, heated to 130° C. in a microwave reactor and stirred for 35 minutes. After cooling to room temperature, the mixture was purified by reverse phase preparative high performance liquid chromatography to obtain the target product 4-((1-(cyclopropylcarbamoyl)indolin-5-yl)oxy)-7-methoxyquinoline-6-carboxamide 1 (64 mg, orange solid), yield: 14%; and 4-((1-(cyclopropylcarbamoyl)indolin-5-yl)oxy)-7-hydroxyquinoline-6-carboxamide 2 (22.3 mg, orange solid), yield: 5%.

4-((1-(Cyclopropylcarbamoyl)indolin-5-yl)oxy)-7-methoxyquinoline-6-carboxamide 1

MS m/z (ESI): 419[M+1]

$^1$H NMR (400 MHz, CD$_3$OD) δ 9.05 (s, 1H), 8.86 (d, J=6.8 Hz, 1H), 8.07 (d, J=8.7 Hz, 1H), 7.59 (s, 1H), 7.20 (d, J=2.3 Hz, 1H), 7.13 (dd, J=8.7, 2.5 Hz, 1H), 6.98 (d, J=6.8 Hz, 1H), 4.22 (s, 3H), 4.00 (t, J=8.7 Hz, 2H), 3.27 (t, J=8.7 Hz, 2H), 2.70-2.63 (m, 1H), 0.80-0.75 (m, 2H), 0.63-0.56 (m, 2H).

4-((1-(Cyclopropylcarbamoyl)indolin-5-yl)oxy)-7-hydroxyquinoline-6-carboxamide 2

MS m/z (ESI): 405[M+H]

$^1$H NMR (400 MHz, CD$_3$OD) δ 9.26 (s, 1H), 8.81 (d, J=6.8 Hz, 1H), 8.08 (d, J=8.8 Hz, 1H), 7.45 (s, 1H), 7.21 (s,

1H), 7.14 (dd, J=8.8, 2.5 Hz, 1H), 6.90 (t, J=5.5 Hz, 1H), 4.00 (t, J=8.7 Hz, 2H), 3.27 (t, J=8.7 Hz, 2H), 2.70-2.63 (m, 1H), 0.81-0.74 (m, 2H), 0.62-0.56 (m, 2H).

Example 3

7-Methoxy-4((1-(methylcarbamoyl)indolin-5-yl)oxy)quinoline-6-carboxamide

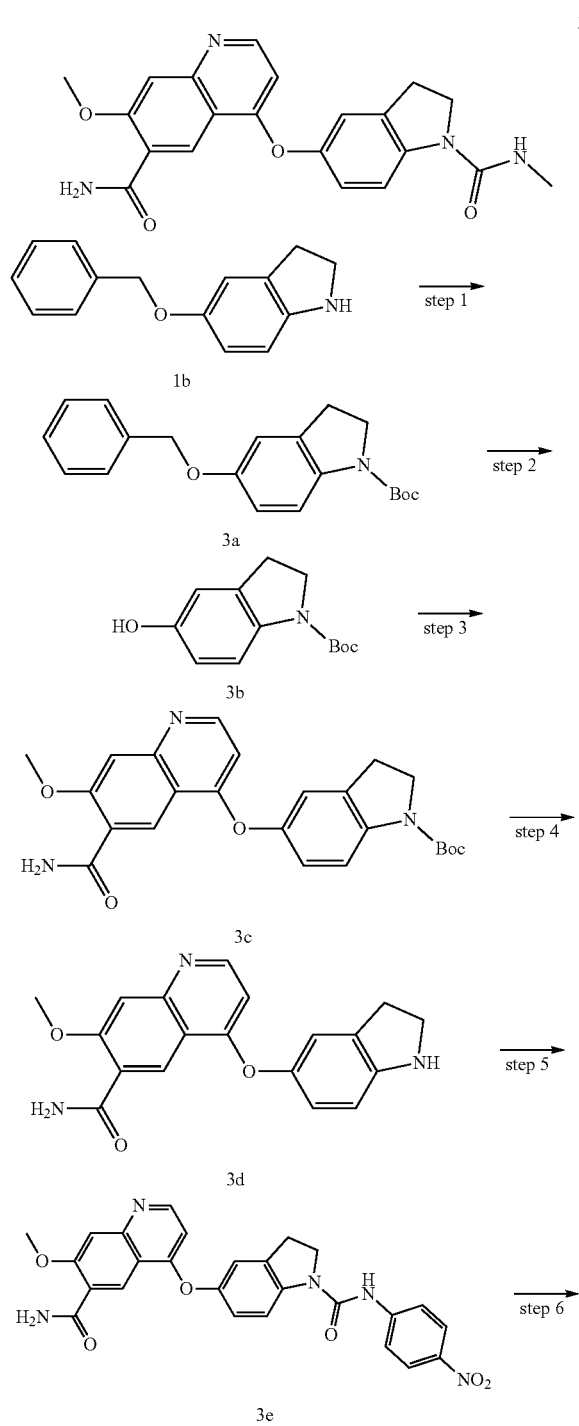

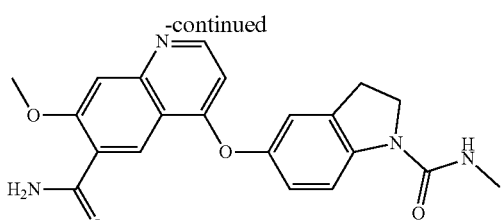

Step 1

Tert-butyl 5-(benzyloxy)indoline-1-carboxylate

Compound 5-(benzyloxy)indoline 1b (2 g, 8.88 mmol) was dissolved in dichloromethane (80 mL), and after cooling to 0° C., triethylamine (1.35 g, 13.32 mmol), 4-dimethylaminopyridine (217 mg, 1.776 mmol) and di-tert-butyl dicarbonate (2.13 g, 9.76 mmol) were added in sequence. After stirring for 2 hours at 0° C., the solvent was removed under reduced pressure, and the residue was purified by silica gel column chromatography (petroleum ether/ethyl acetate=2/1) to obtain the target product tert-butyl 5-(benzyloxy)indoline-1-carboxylate 3a (2.42 g, white solid), yield: 42%.

MS m/z (ESI): 270[M+1-56]

$^1$H NMR (400 MHz, CDCl$_3$) δ 7.74 (s, 1H), 7.44-7.28 (m, 5H), 6.80 (s, 1H), 6.77 (d, J=8.7 Hz, 1H), 5.02 (s, 2H), 3.96 (s, 2H), 3.04 (t, J=8.7 Hz, 2H), 1.55 (s, 9H).

Step 2

Tert-butyl 5-hydroxyindoline-1-carboxylate

Compound tert-butyl 5-(benzyloxy)indoline-1-carboxylate 3a (2.42 g, 7.44 mmol) was dissolved in methanol (80 mL), then 10% palladium on carbon (1.2 g) was added, and the mixture was stirred under a hydrogen atmosphere at room temperature for 2 hours. The reaction was filtered after it completed, and the solvent was removed from the filtrate under reduced pressure to obtain the target product tert-butyl 5-hydroxyindoline-1-carboxylate 3b (1.65 g, gray solid), yield 95%.

MS m/z (ESI): 180[M+1-56]

$^1$H NMR (400 MHz, CDCl$_3$) δ 7.69 (s, 1H), 6.67 (s, 1H), 6.62 (dd, J=8.6, 2.2 Hz, 1H), 4.81 (s, 1H), 3.96 (s, 2H), 3.03 (t, J=8.6 Hz, 2H), 1.55 (s, 9H).

Step 3

Tert-butyl 5-((6-carbamoyl-7-methoxyquinolin-4-yl)oxy)indoline-1-carboxylate

Compound tert-butyl 5-hydroxyindoline-1-carboxylate 3b (590 mg, 2.5 mmol), 4-chloro-7-methoxyquinoline-6-carboxamide (590 mg, 2.5 mmol), potassium tert-butoxide (340 mg, 3 mmol) and dimethyl sulfoxide (10 mL) were mixed, heated to 65° C. and stirred for 16 hours. After cooling to room temperature, water (50 mL) was added. After stirring for 20 minutes, the reaction was filtered, and the solid was dried in air to obtain the target product tert-butyl 5-((6-carbamoyl-7-methoxyquinolin-4-yl)oxy)indoline-1-carboxylate 3c (1.01 g, gray solid), yield: 93%.

MS m/z (ESI): 436[M+1]

$^1$H NMR (400 MHz, CDCl$_3$) δ 9.31 (s, 1H), 8.62 (d, J=5.4 Hz, 1H), 7.92 (s, 1H), 7.77 (s, 1H), 7.59 (s, 1H), 6.97 (d,

J=6.4 Hz, 2H), 6.47 (d, J=5.4 Hz, 1H), 5.91 (s, 1H), 4.13 (s, 3H), 4.06 (t, J=8.4 Hz, 2H), 3.13 (t, J=8.7 Hz, 2H), 1.58 (s, 9H).

Step 4

4-(Indolin-5-oxy)-7-methoxyquinoline-6-carboxamide

Compound tert-butyl 5((6-carbamoyl-7-methoxyquinolin-4-yl)oxy) indoline-1-carboxylate 3c (1.01 g, 2.32 mmol) was dissolved in dichloromethane (20 mL), then trifluoroacetic acid (8 mL) was added dropwise. After stirring for 2 hours at room temperature, the solvent was removed under reduced pressure. The residue was dispersed into saturated sodium bicarbonate solution (50 mL), and then extracted with dichloromethane (50 mL×3). The organic phases were combined, and then dried over anhydrous sodium sulfate. After filtration, the solvent was removed from the filtrate under reduced pressure. The residue was purified by silica gel column chromatography (dichloromethane/methanol=10/1) to obtain the target product 4-(indolin-5-oxy)-7-methoxyquinoline-6-carboxamide 3d (713 mg, yellow solid), yield: 92%.

MS m/z (ESI): 336[M+1]

Step 5

4-Nitrophenyl 5-((6-carbamoyl-7-methoxyquinolin-4-yl)oxy)indoline-1-carboxylate

Compound 4-(indolin-5-oxy)-7-methoxyquinoline-6-carboxamide 3d (107 mg, 0.32 mmol) was dissolved in tetrahydrofuran (5 mL), and after cooling to 0° C., p-nitrophenyl chloroformate (64 mg, 0.32 mmol) was added. After stirring for 30 minutes at room temperature, the reaction was quenched with saturated sodium bicarbonate solution (20 mL), and then extracted with dichloromethane (20 mL×2). The organic phases were combined, and then dried over anhydrous sodium sulfate. After filtration, the solvent was removed from the filtrate under reduced pressure. The residue was purified by silica gel column chromatography (dichloromethane/methanol=50/1) to obtain the target product 4-nitrophenyl 54(6-carbamoyl-7-methoxyquinolin-4-yl) oxy)indoline-1-carboxylate 3e (110 mg, white solid), yield: 69%.

MS m/z (ESI): 501[M+1]

Step 6

7-Methoxy-4-((1-(methylcarbamoyl)indolin-5-yl) oxy)quinoline-6-carboxamide

Compound 4-nitrophenyl 5((6-carbamoyl-7-methoxyquinolin-4-yl) oxy)indoline-1-carboxylate 3e (110 mg, 0.22 mmol) was dissolved in tetrahydrofuran (8 mL), then methylamine in tetrahydrofuran (2 M, 2 mL, 4 mmol) was added, and the mixture was heated in a sealed tube at 80° C. for 1 hour. After cooling to room temperature, the solvent was removed under reduced pressure, and the residue was purified by reverse-phase preparative high performance liquid chromatography to obtain the target product 7-methoxy-4-((1-(methylcarbamoyl)indolin-5-yl)oxy)quinoline-6-carboxamide 3 (42 mg, yellow solid), yield: 44%.

MS M/Z (ESI): 393[M+1]

$^1$H NMR (400 MHz, CD$_3$OD) δ 9.06 (s, 1H), 8.87 (d, J=6.8 Hz, 1H), 8.06 (d, J=8.7 Hz, 1H), 7.58 (s, 1H), 7.21 (s, 1H), 7.13 (dd, J=8.6, 2.3 Hz, 1H), 7.00 (d, J=6.8 Hz, 1H), 4.23 (s, 3H), 4.03 (t, J=8.7 Hz, 2H), 3.28 (d, J=8.7 Hz, 2H), 2.86 (s, 3H).

Example 4

4-((1-((4-Fluorophenyl)carbamoyl)indolin-5-yl) oxy)-7-methoxyquinoline-6-carboxamide

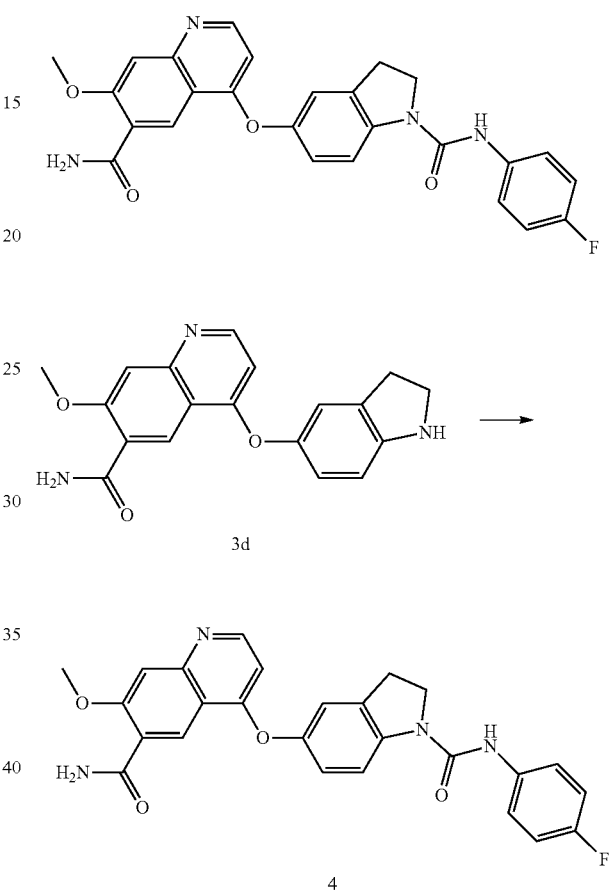

Compound p-nitrophenyl chloroformate (40 mg, 0.2 mmol) was dissolved in tetrahydrofuran (5 mL), and after cooled to 0° C., 4-fluoroaniline (22 mg, 0.2 mmol) was added. After warming to room temperature and stirring for 1 hour, 4-(indolin-5-oxy)-7-methoxyquinoline-6-carboxamide 3d (70 mg, 0.21 mmol) and diisopropylethylamine (97 mg, 0.75 mmol) were added, then the mixture was heated to 80° C. in a microwave reactor and stirred for 1 hour. After cooling to room temperature, the solvent was removed under reduced pressure, and the residue was purified by reverse-phase preparative high performance liquid chromatography to obtain the target product 4-((1-((4-fluorophenyl)carbamoyl)indolin-5-yl)oxy)-7-methoxyquinoline-6-carboxamide 4 (24 mg, yellow solid), yield: 23%.

MS m/z (ESI): 473[M+1]

$^1$H NMR (400 MHz, CD$_3$OD) δ 9.06 (s, 1H), 8.89 (d, J=6.8 Hz, 1H), 8.09 (d, J=8.8 Hz, 1H), 7.60 (s, 1H), 7.54-7.47 (m, 2H), 7.26 (d, J=2.1 Hz, 1H), 7.16 (dd, J=8.8, 2.5 Hz, 1H), 7.09 (t, J=8.8 Hz, 2H), 7.02 (d, J=6.8 Hz, 1H), 4.27 (t, J=8.7 Hz, 2H), 4.23 (s, 3H), 3.37 (t, J=8.6 Hz, 2H).

Example 5

N-Cyclopropyl-5-((6,7-dimethoxyquinolin-4-yl)oxy)indoline-1-carboxamide

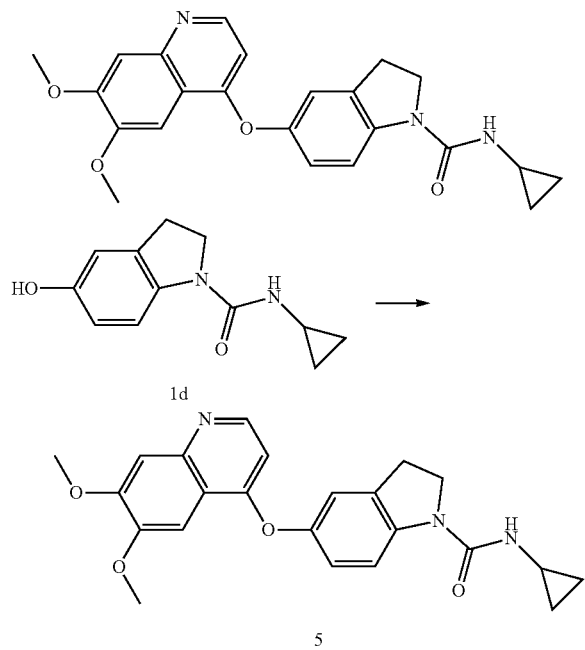

Compound N-cyclopropyl-5-hydroxyindoline-1-carboxamide 1d (200 mg, 0.917 mmol), 4-chloro-6,7-dimethoxyquinoline (200 mg, 0.897 mmol), potassium tert-butoxide (300 mg, 2.75 mmol) and N,N-dimethylformamide (3 mL) were mixed, heated to 70° C. and stirred for 12 hours. After cooling to room temperature, the mixture was purified by reverse phase preparative high performance liquid chromatography to obtain the target product N-cyclopropyl-5-((6,7-dimethoxyquinolin-4-yl)oxy)indoline-1-carboxamide 1 (50 mg, yellow solid), yield: 13%.

MS m/z (ESI): 406[M+1]

$^1$H NMR (400 MHz, DMSO-d$_6$) δ 8.80 (d, J=6.7 Hz, 1H), 8.00 (d, J=8.7 Hz, 1H), 7.74 (s, 1H), 7.73-7.68 (m, 1H), 7.22 (d, J=2.4 Hz, 1H), 7.12 (dd, J=8.7, 2.5 Hz, 1H), 6.85 (s, 1H), 6.84 (s, 1H), 4.04 (s, 3H), 4.04 (s, 3H), 3.93 (t, J=8.7 Hz, 2H), 3.16 (t, J=8.6 Hz, 2H), 2.66-2.57 (m, 1H), 0.67-0.60 (m, 2H), 0.54-0.47 (m, 2H).

Example 6

7-Methoxy-4-((1-((5-methylisoxazol-3-yl)carbamoyl)indolin-5-yl)oxy)quinoline-6-carboxamide

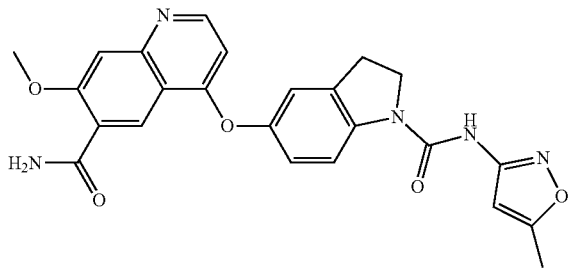

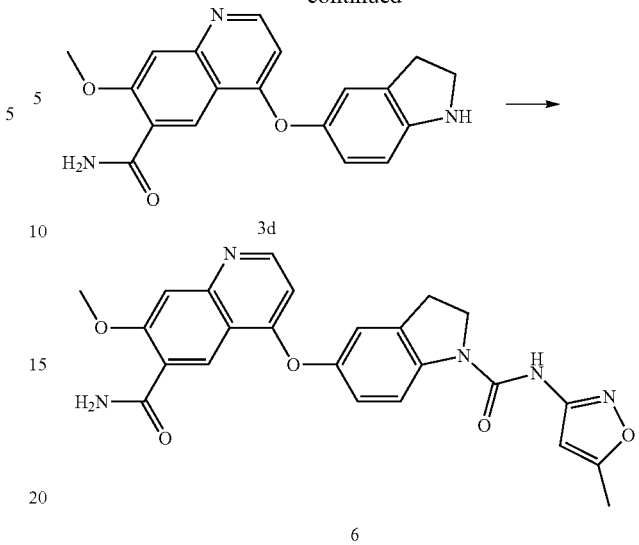

Compound 5-methylisoxazole-3-amine (98 mg, 1.0 mmol) was dissolved in anhydrous tetrahydrofuran (2 mL), and then pyridine (0.2 mL) and phenyl chloroformate (156 mg, 1.0 mmol) were added sequentially. After stirring for 2 hours at room temperature, the solvent was removed under reduced pressure. The residue was dissolved in ethyl acetate (20 mL), washed with water (5 mL×2), and then dried over anhydrous sodium sulfate. After filtration, the solvent was removed from the filtrate under reduced pressure to obtain an off-white solid. The solid and 4-(indolin-5-oxy)-7-methoxyquinoline-6-carboxamide 3d (80 mg, 0.24 mmol) were dissolved together in N,N-dimethylformamide (1 mL), and then 4-dimethylaminopyridine (1 mg, 0.082 mmol) was added. After stirring for 40 hours at room temperature, the solvent was removed under reduced pressure, and the residue was purified by reverse phase preparative high performance liquid chromatography to obtain the target product 7-methoxy-4-(04(5-methylisoxazol-3-yl)carbamoypindolin-5-yl) oxy)quinoline-6-carboxamide 6 (47 mg, yellow solid), yield: 43%.

MS m/z (ESI): 460[M+1]

$^1$H NMR (400 MHz, DMSO-d$_6$) δ 9.80 (s, 1H), 8.96 (d, J=6.4 Hz, 1H), 8.75 (s, 1H), 8.02 (d, J=8.7 Hz, 1H), 7.97 (s, 1H), 7.90 (s, 1H), 7.76 (s, 1H), 7.30 (s, 1H), 7.20 (d, J=7.9 Hz, 1H), 6.86 (d, J=6.4 Hz, 1H), 6.61 (s, 1H), 4.23 (t, J=8.3 Hz, 2H), 4.09 (s, 3H), 3.24 (t, J=8.1 Hz, 2H), 2.39 (s, 3H).

Biological Experiment

VEGFR1 Activity Inhibition Testing

An in vitro kinase assay was used to evaluate the effect of the compounds of the present invention on VEGFR1 activity.

The experimental method is summarized as follows:

The in vitro activity of VEGFR1 was determined by detecting the phosphorylation level of the substrate in the kinase reaction using a homogeneous time-resolved fluorescence (HTRF) kinase detection kit (Cisbio, catalog number 62TKOPEC). The reaction buffer contains an enzyme reaction buffer (1×) provided in the kit, 5 mM MgCl$_2$, 1 mM MnCl$_2$, 1 mM DTT. The humanized recombinant VEGFR1 protein (Cat. No. PV3666) was purchased from ThermoFish, and diluted to a 0.3 ng/μL kinase solution with the reaction buffer. The substrate reaction solution includes 1 μM biotin-labeled tyrosine kinase substrate and 0.8 μM ATP which were diluted with the reaction buffer. The assay buffer includes 0.1 ng/µL Eu$^{3+}$ labeled cage antibody and 0.125 µM streptavidin labeled XL665 which were diluted with the reaction buffer.

The compound was dissolved and diluted to 10 µM in 100% DMSO, then a 4-fold serial dilution was performed with DMSO to the lowest concentration of 0.61 nM, and each concentration point was diluted 40-fold with the reaction buffer.

4 µL of Compound solution and 2 µL of VEGFR1 kinase solution were added to a 384-well detection plate (Corning, catalog number 4512), mixed uniformly and incubated at room temperature for 15 minutes. Then 4 µL of the substrate reaction solution was added, and the reaction mixture was incubated at room temperature for 50 minutes. Then 10 µL of the assay buffer equal to the volume of the reaction was added, mixed uniformly and allowed to stand at room temperature for 30 minutes, and then the reaction progress was detected with an Envision plate reader (Perkin Elmer) at wavelengths of 620 nm and 665 nm. The ratio of 665/620 is positively correlated with the phosphorylation degree of the substrate, thereby detecting the activity of VEGFR1 kinase. In this experiment, the group without VEGFR1 kinase protein was used as a negative control (100% inhibition), and the group with VEGFR1 kinase protein but no compound was used as a positive control (0% inhibition). The inhibition percentage of the compound on VEGFR1 activity can be calculated using the following equation:

Percentage of inhibition=100−100*(signal value of test compound at a specific concentration−signal value of negative control)/(signal value of positive control−signal value of negative control)

The IC$_{50}$ value of the compound is calculated from 8 concentration points with the XLfit (ID Business Solutions Ltd., UK) software through the following equation:

$$Y=\text{Bottom}+(\text{Top}-\text{Bottom})/(1+10^{((\log IC_{50}-X)*\text{slope factor})})$$

where Y is the inhibition percentage, X is the logarithm of the concentration of the test compound, Bottom is the maximum inhibition percentage, Top is the minimum inhibition percentage, and slope factor is the slope coefficient of the curve.

VEGFR2 Activity Inhibition Testing

An in vitro kinase assay was used to evaluate the effect of the compounds of the present invention on VEGFR2 activity.

The experimental method is summarized as follows:

The in vitro activity of VEGFR2 was determined by detecting the phosphorylation level of the substrate in the kinase reaction using a homogeneous time-resolved fluorescence (HTRF) kinase detection kit (Cisbio, catalog number 62TKOPEC). The reaction buffer contains an enzyme reaction buffer (1×) provided in the kit, 5 mM MgCl$_2$, 1 mM MnCl$_2$, 1 mM DTT, 0.01% BSA and 0.005% Tween 20. The humanized recombinant VEGFR2 protein (Cat. No. 10012-H20B1) was purchased from Sino Biological Inc., and diluted to a 0.3 ng/µL kinase solution with the reaction buffer. The substrate reaction solution includes 0.3 µM biotin-labeled tyrosine kinase substrate and 3.5 µM ATP which were diluted with the reaction buffer. The assay buffer includes 0.1 ng/µL Eu$^{3+}$ labeled cage antibody and 18.75 nM streptavidin labeled XL665 (Cisbio, catalog number 610SAXLB) which were diluted with the reaction buffer.

The compound was dissolved and diluted to 10 µM in 100% DMSO, then a 4-fold serial dilution was performed with DMSO to the lowest concentration of 0.61 nM, and each concentration point was diluted 40-fold with the reaction buffer.

4 µL of Compound solution and 2 µL of VEGFR2 kinase solution were added to a 384-well detection plate (Corning, catalog number 4512), mixed uniformly and incubated at room temperature for 15 minutes. Then 4 µL of the substrate reaction solution was added, and the reaction mixture was incubated at room temperature for 30 minutes. Then 10 µL of the assay buffer equal to the volume of the reaction was added, mixed uniformly and allowed to stand at room temperature for 30 minutes, and then the reaction progress was detected with an Envision plate reader (Perkin Elmer) at wavelengths of 620 nm and 665 nm. The ratio of 665/620 is positively correlated with the phosphorylation degree of the substrate, thereby detecting the activity of VEGFR2 kinase. In this experiment, the group without VEGFR2 kinase protein was used as a negative control (100% inhibition), and the group with VEGFR2 kinase protein but no compound was used as a positive control (0% inhibition). The inhibition percentage of the compound on VEGFR2 activity can be calculated using the following equation:

Percentage of inhibition=100−100*(signal value of test compound at a specific concentration−signal value of negative control)/(signal value of positive control—signal value of negative control)

The IC$_{50}$ value of the compound is calculated from 8 concentration points with the XLfit (ID Business Solutions Ltd., UK) software through the following equation:

$$Y=\text{Bottom}+(\text{Top}-\text{Bottom})/(1+10^{((\log IC_{50}-X)*\text{slope factor})})$$

where Y is the inhibition percentage, X is the logarithm of the concentration of the test compound, Bottom is the maximum inhibition percentage, Top is the minimum inhibition percentage, and slope factor is the slope coefficient of the curve.

VEGFR3 Activity Inhibition Testing

An in vitro kinase assay was used to evaluate the effect of the compounds of the present invention on VEGFR3 activity.

The experimental method is summarized as follows:

The in vitro activity of VEGFR3 was determined by detecting the phosphorylation level of the substrate in the kinase reaction using a HTRF kinase detection kit (Cisbio, catalog number 62TK0PEC). The reaction buffer contains an enzyme reaction buffer (1×) provided in the kit, 5 mM MgCl$_2$, 1 mM MnCl$_2$, 1 mM DTT and 0.01% Tween 20. The humanized recombinant VEGFR3 protein (Cat. No. 08-190) was purchased from Carna Biosciences, and diluted to a 0.05 ng/µL kinase solution with the reaction buffer. The substrate reaction solution includes 0.13 µM biotin-labeled tyrosine kinase substrate and 0.4 µM ATP which were diluted with the reaction buffer. The assay buffer includes 0.1 ng/µL Eu$^{3+}$ labeled cage antibody and 8.13 nM streptavidin labeled XL665 which were diluted with the reaction buffer.

The compound was dissolved and diluted to 10 µM in 100% DMSO, then a 4-fold serial dilution was performed with DMSO to the lowest concentration of 0.61 nM, and each concentration point was diluted 40-fold with the reaction buffer.

4 µL of Compound solution and 2 µL of VEGFR3 kinase solution were added to a 384-well detection plate (Corning, catalog number 4512), mixed uniformly and incubated at room temperature for 15 minutes. Then 4 µL of the substrate reaction solution was added, and the reaction mixture was incubated at room temperature for 40 minutes. Then 10 μL of the assay buffer equal to the volume of the reaction was added, mixed uniformly and allowed to stand at room temperature for 30 minutes, and then the reaction progress was detected with an Envision plate reader (Perkin Elmer) at wavelengths of 620 nm and 665 nm. The ratio of 665/620 is positively correlated with the phosphorylation degree of the substrate, thereby detecting the activity of VEGFR3 kinase. In this experiment, the group without VEGFR3 kinase protein was used as a negative control (100% inhibition), and the group with VEGFR3 kinase protein but no compound was used as a positive control (0% inhibition). The inhibition percentage of the compound on VEGFR3 activity can be calculated using the following equation:

Percentage of inhibition=100−100*(signal value of test compound at a specific concentration−signal value of negative control)/(signal value of positive control−signal value of negative control)

The $IC_{50}$ value of the compound is calculated from 8 concentration points with the XLfit (ID Business Solutions Ltd., UK) software through the following equation:

$Y$=Bottom+(Top−Bottom)/(1+10^((log $IC_{50}$−$X$)*slope factor))

where Y is the inhibition percentage, X is the logarithm of the concentration of the test compound, Bottom is the maximum inhibition percentage, Top is the minimum inhibition percentage, and slope factor is the slope coefficient of the curve.

The activity data for some representative example compounds are listed as follows:

| Compound No. | VEGFR1 | $IC_{50}$ VEGFR2 | VEGFR3 |
|---|---|---|---|
| 1 | B | A | A |
| 2 |   | B |   |
| 3 |   | B |   |
| 4 |   | A |   |
| 5 |   | B |   |
| 6 |   | A |   |

A < 10 nM; 10 nM ≤ B < 100 nM

The example compounds of the invention respectively have a significant inhibitory effect on the activity of VEGFR.

The invention claimed is:

1. A compound, or a pharmaceutically acceptable salt, stable isotope derivative, isomer thereof or mixture thereof, wherein the compound is selected from:

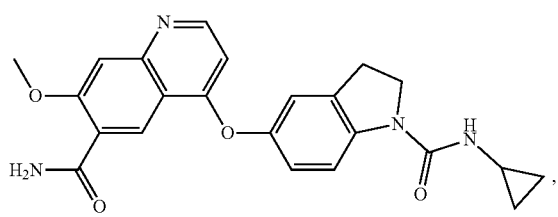

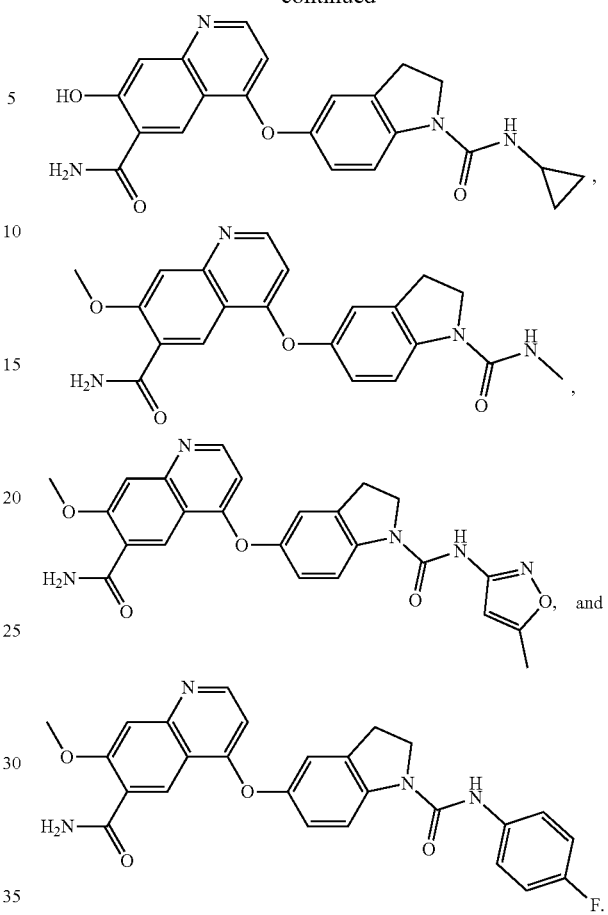

2. A pharmaceutical composition comprising a compound according to claim 1, or a pharmaceutically acceptable salt, stable isotope derivative, isomer thereof or mixture thereof, and a pharmaceutically acceptable carrier and excipient.

3. A pharmaceutical composition comprising a compound according to claim 1, or a pharmaceutically acceptable salt, stable isotope derivative, isomer thereof or mixture thereof, and at least one additional drug, wherein the at least one additional drug is a chemotherapeutic agent or an immunomodulator.

4. A method of treating or preventing a VEGFR-mediated disease in a subject, the method comprising administering to the subject a therapeutically effective amount of the compound of claim 1.

5. The pharmaceutical composition of claim 3, wherein the chemotherapeutic agent or the immunomodulator is an immune checkpoint inhibitor.

6. The method of claim 4, wherein the VEGFR-mediated disease is a tumor.

* * * * *